United States Patent
Yoo et al.

(10) Patent No.: US 9,055,904 B2
(45) Date of Patent: Jun. 16, 2015

(54) MULTI-TOUCH DISPLAY AND INPUT FOR VISION TESTING AND TRAINING

(75) Inventors: Herb Yoo, Beaverton, OR (US); Thomas R. Fortune, Jr., Aloha, OR (US); Douglas Pedley, Portland, OR (US); Alan W. Reichow, Beaverton, OR (US); Matthew Genar Hilla, Portland, OR (US); Rick M. Rezinas, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 1202 days.

(21) Appl. No.: 12/534,605

(22) Filed: Aug. 3, 2009

(65) Prior Publication Data
US 2011/0025611 A1 Feb. 3, 2011

(51) Int. Cl.
*A61B 3/00* (2006.01)
*A61B 5/16* (2006.01)
(Continued)

(52) U.S. Cl.
CPC ............. *A61B 5/16* (2013.01); *A61B 3/0016* (2013.01); *A61B 3/0041* (2013.01); *A61B 3/0033* (2013.01); *A61B 3/024* (2013.01);
(Continued)

(58) Field of Classification Search
CPC ...... A61B 3/00; A61B 3/0016; A61B 3/0033; A61B 3/0041; A61B 3/005; A61B 3/0058; A61B 3/0066; A61B 3/0075; A61B 3/02; A61B 3/024; A61B 3/028; A61B 3/032; A61B 3/18; A61B 3/185; A61B 5/00; A61H 2205/024
USPC .......... 345/7–9; 351/203, 209, 200, 218, 222, 351/223; 715/700
See application file for complete search history.

(56) References Cited

U.S. PATENT DOCUMENTS 5,589,897 A * 12/1996 Sinclair et al. ................ 351/223
5,825,460 A * 10/1998 Kohayakawa ................ 351/237
(Continued)

FOREIGN PATENT DOCUMENTS

| CN | 101057172 | 10/2007 |
| WO | 2006025056 A2 | 3/2006 |
| WO | 2008128183 A1 | 10/2008 |

OTHER PUBLICATIONS

EPO Supplementary Search Report No. 126046GB dated Nov. 5, 2013 in European patent application No. 10807030.1.
(Continued)

*Primary Examiner* — Jason Mandeville
(74) *Attorney, Agent, or Firm* — Shook, Hardy & Bacon L.L.P.

(57) ABSTRACT

The present invention provides systems and methods for receiving an input to a sensory test or training activity by way of a touch-screen device. The touch-screen device receives instructions by way of a wireless communication protocol from a sensory testing and training device. The instructions may be comprised of a command to display a graphical element on the touch-screen device. As a result, the touch-screen device displays the graphical element on a display surface of the touch-screen device. Further, an input may be received from a subject in the form of a physical contact between the subject and the display surface of the touch-screen device. The input may be in response to a sensory test or a sensory training activity. Additionally, the touch-screen device communicates the input to the sensory training device utilizing a wireless communication protocol. In an additional embodiment, the touch-screen device provides feedback to a user.

19 Claims, 7 Drawing Sheets

(51) Int. Cl.

| | | |
|---|---|---|
| *A61B 3/024* | (2006.01) | |
| *A61B 3/032* | (2006.01) | |
| *A61B 5/11* | (2006.01) | |
| *A61H 5/00* | (2006.01) | |
| *G06F 19/00* | (2011.01) | |
| *A61B 3/028* | (2006.01) | |

(52) U.S. Cl.
CPC ............... *A61B 3/028* (2013.01); *A61B 3/032* (2013.01); *A61B 5/1124* (2013.01); *A61H 5/00* (2013.01); *A61H 2201/5046* (2013.01); *G06F 19/3406* (2013.01); *G06F 19/3418* (2013.01)

(56) References Cited

U.S. PATENT DOCUMENTS

| | | | | |
|---|---|---|---|---|
| 6,364,845 | B1 * | 4/2002 | Duffy et al. | 600/558 |
| 6,533,417 | B1 * | 3/2003 | Sain | 351/203 |
| 7,101,044 | B2 * | 9/2006 | Fink | 351/211 |
| 7,350,921 | B2 * | 4/2008 | Ridings | 351/237 |
| 7,367,675 | B2 * | 5/2008 | Maddalena et al. | 351/237 |
| 7,537,343 | B2 * | 5/2009 | Kanazawa et al. | 351/239 |
| 7,663,607 | B2 * | 2/2010 | Hotelling et al. | 345/173 |
| 7,690,790 | B2 * | 4/2010 | Hosoi et al. | 351/242 |
| 8,047,652 | B1 * | 11/2011 | Collazo | 351/223 |
| 2005/0225720 | A1 | 10/2005 | Ridings | |
| 2006/0066448 | A1 | 3/2006 | Berisford et al. | |
| 2008/0309616 | A1 * | 12/2008 | Massengill | 345/156 |
| 2008/0309879 | A1 | 12/2008 | Hirji | |
| 2009/0002217 | A1 | 1/2009 | Kryze et al. | |
| 2009/0158203 | A1 | 6/2009 | Kerr et al. | |

OTHER PUBLICATIONS

Japanese Office Action Summary, Patent Application No. 2012-523699 dated Jun. 3, 2014, 5 pages.
European Office Action dated Nov. 26, 2014 in European Application No. 10807030.1, 5 pages.
International Search Report and Written Opinion, International Application PCT/US10/44256, 11 pages, Mailed Sep. 23, 2010.

* cited by examiner

MULTI-TOUCH DISPLAY AND INPUT FOR VISION TESTING AND TRAINING

TECHNICAL FIELD

The present invention relates generally to methods and systems utilizing a multi-touch display as an input for testing and training of sensory abilities of individuals.

BACKGROUND

A large number of sensory tests may be performed to determine strengths and weaknesses of an individual's sensory abilities. Typically, such tests are applied to determine whether an individual may benefit from some form of sensory correction and/or training and, if so, what type and degree of sensory correction and/or training may be desirable.

SUMMARY

The present invention provides systems and methods for receiving an input to a sensory test by way of a touch-screen device. The touch-screen device receives instructions by way of a wireless communication protocol from a sensory testing and training device. The instructions are comprised of a command to display a graphical element on the touch-screen device. As a result, the touch-screen device displays the graphical element on a display surface of the touch-screen device. Further, an input is received from a subject in the form of a physical contact between the subject and the display surface of the touch-screen device. The input is in response to a sensory test or a sensory training activity. Additionally, the touch-screen device communicates the input to the sensory training device utilizing a wireless communication protocol.

It should be noted that this Summary is provided to generally introduce the reader to one or more select concepts described below in the Detailed Description in a simplified form. This Summary is not intended to identify key assessment and/or required features of the claimed subject matter, nor is it intended to be used as an aid in determining the scope of the claimed subject matter.

BRIEF DESCRIPTION OF THE DRAWINGS

The present invention is described in detail below with reference to the attached drawing figures, which are incorporated by reference herein and wherein.

DETAILED DESCRIPTION

Figure 1:
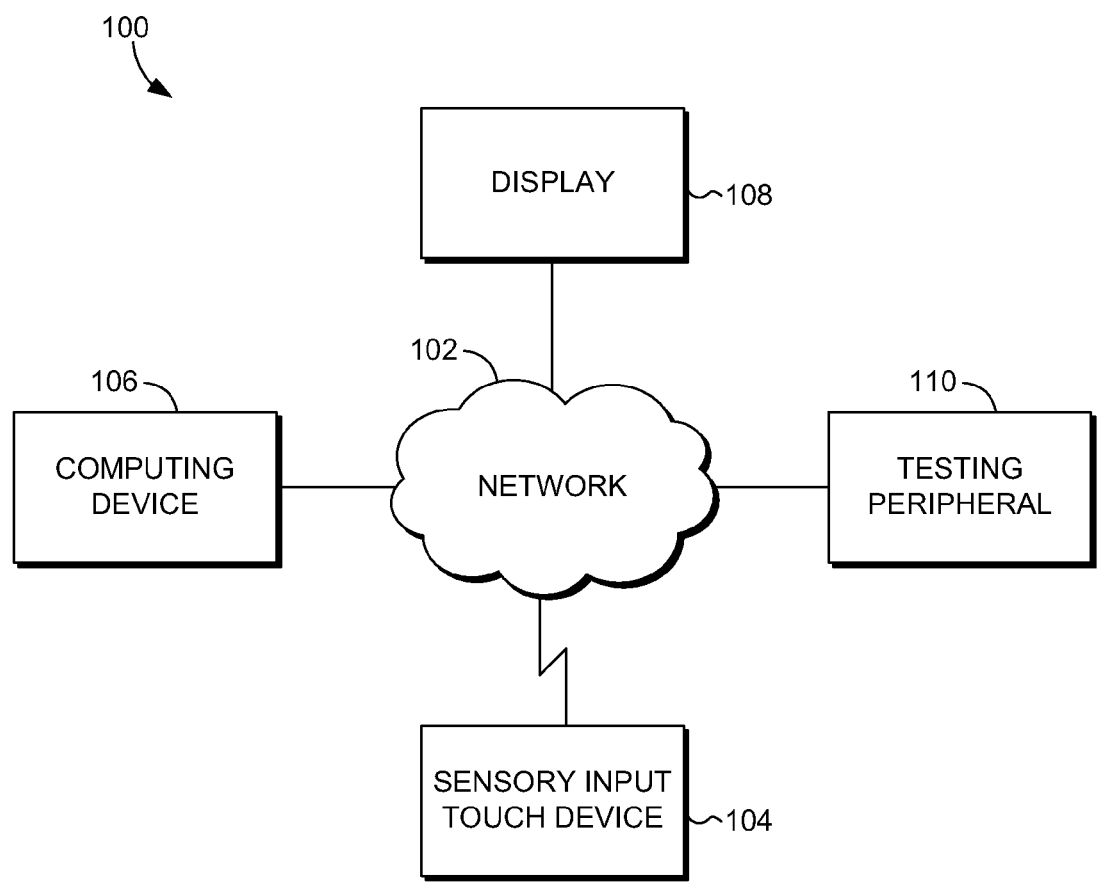
FIG. 1 illustrates a system in accordance with embodiments of the present invention.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Embodiments of the present invention relate to systems, methods, and computer storage media for receiving an input to a sensory test by way of a touch-screen device having memory and a processor. The method may comprise receiving instruction by way of a wireless communication protocol from a sensory testing and training device. The instructions are comprised of a command to display a graphical element on the touch-screen device. The method may also include displaying the graphical element on a display surface of the touch-screen device. The method may additionally include receiving an input from a subject in the form of a physical contact between the subject and the display surface of the touch-screen device. The input is in response to a sensory test or a sensory training activity. The method may also include communicating the input to the sensory training device utilizing the wireless communication protocol.

A second method in accordance with the present invention may comprise wirelessly receiving an input in response to a sensory training activity from a subject at a touch-screen device. The method may include displaying on a display moveably mounted to a sensory testing and training device, a graphical element used in the sensory training activity. The method may also include receiving the input from a subject at the touch-screen device, wherein the input is a directional indication as determined from a physical contact between the subject and the touch-screen device within about 15 degrees of an orthogonal axis of the touch-screen device. The method may also include determining a command based on the input; processing the command; and communicating a feedback to the touch-screen device, wherein the feedback is processed by the touch-screen device to provide visual or audible feedback to the subject in response to the input.

A system in accordance with the present invention may comprise a sensory testing and training device having a processor and memory for facilitating a sensory test or a sensory training activity. The sensory testing and training device is further comprised of a wireless communication component for communicating with a touch-screen device. The system may also include a touch-screen device having a processor and memory for receiving an input from a subject in response to the sensory test or sensory training activity. The touch-screen device is functional to communicate wirelessly with the sensory testing and training device.

Sensory testing gathers data on a subject's current sensory ability. Sensory ability may refer to a subject's sensory ability, perceptual ability, cognitive ability, visual ability, auditory ability, etc. The specific tests administered to a subject will vary depending on the individual's ability, desired activity, and competitive level. Using such tests, it may be determined during the assessment that the individual has a particular weakness and/or strength in a different aspect of his sensory ability. Given this weakness, a training program may be created to train the individual on that weakness. For example, if an individual's saccadic and peripheral visual ability is weak; various baseline measurements will be analyzed during the assessment to determine such a weakness. Alternatively, if, after testing and assessing, it is determined that an individual has focusing problems at specific gaze angles, that skill may then be trained.

Generally, the data collected from each subject may include demographic information, static sensory data, dynamic sensory data, and, optionally, health data. Demographic information may include the individual's name, gender, primary activity, evaluation level, and the like. Static sensory data may include, for example, measurements of the individual's standard vision, static visual acuity, contrast sensitivity, depth perception, etc. Dynamic sensory data may include eye-hand coordination, dynamic visual acuity, split attention, eye-body coordination, dynamic tracking, etc. Examples of health data may include the dates of the previous examinations, gender, weight, age, etc. Once the testing has occurred, the data may be reviewed (e.g., by the trainer administering the testing) to verify the data prior to transferring the data to a central location. That is, the data may receive an initial check for obvious errors in case more testing is required.

A sensory input touch device may be used by a testing administrator, a subject, or a third party to enter, receive, and/or communicate the various data. For example, a sensory testing and training device may present a vision test comprised of a plurality of graphical elements that are viewed by a test subject. Depending on the various graphical elements displayed, the subject may provide an input in response to the graphical elements. For example, a Landolt C may be displayed as one of the visual elements that the subject needs to identify the location of a gap within the Landolt C. The subject may provide an indication as to the location of the gap by physically contacting a touch screen of a sensory input touch device. The physical contact may comprise the subject placing a finger on the touch screen and sliding the finger in a direction equivalent to the location of the gap. For example, if the Landolt C that is displayed has a gap on the right side (e.g., three o'clock position), the subject may place a finger on the touch screen and slide the finger from the original contact point in a direction to the right on the touch screen. Therefore, the sliding of a finger to the right may provide an input as to the subject's perception that the Landolt C has a gap on the right side.

The distance at which some sensory tests are performed affects the reliability, repeatability, precision, and accuracy of the test. Therefore, some sensory skill tests and training exercises are performed at predefined distances. For example, a sensory testing and training device may include a display for presenting one or more graphical elements as part of a sensory test or training activity. The subject to which the test or training activity is being administered may be required to be a specified distance from the display. In such a circumstance, it may be beneficial for the subject to have an input device that is capable of wirelessly communicating the subject's input to one or more computing devices associated with the sensory testing and training device. In an exemplary embodiment, a touch-screen device that is able to receive an input from a subject, identify the intent of the input, and communicate the intent to a testing device without the burden of cable or tethers.

Additionally, some sensory tests require a subject to focus on the sensory test or training activity while still providing an input. As a result, an intuitive input device may be desired that allows the subject to maintain focus on a test or training activity while still providing valuable input in response to the testing or training activity. In an exemplary embodiment, a touch-screen device allows a subject to provide an input in a general area (e.g., quadrant of a display surface, portion of a display surface) without requiring the subject to divert a portion of their attention to locate a specific button, key, or indication to provide an input. For example, a touch screen may be advantageous in some embodiments when a user is required to provide an indication as to up, down, left, or right. In such an embodiment the subject may contact the touch screen in a general area of the screen corresponding to a desired input (e.g., touch the top of the screen for an up indication, touch the right side of the touch screen for a right indication). In an additional embodiment, the subject may contact a touch screen at a point and then drag (e.g., slide) an object or finger in the desired direction they wish to indicate (e.g., slide a stylus from the original point of contact to the right to indicate a "right" input). As a result, a subject may maintain focus and concentration on a sensory test or training activity to which they are providing an input.

A touch screen that serves as an input device for a sensory test or sensory training activity may also be advantageous as it may alter one or more displayed graphics to guide the subject in providing input. For example, a touch screen may change displayed elements to coincide with a particular sensory test being administered to a subject.

Additionally, some sensory tests may require a subject to receive sensory stimulation from two or more locations. For example, a near-far vision test may require the subject to view one or more graphical elements at a predefined distance from the subject and then view one or more graphical elements at a closer predefined distance from the subject. In an exemplary embodiment, it may be desirable to incorporate an input device and a sensory stimulation device. For example, returning to the near-far vision test, the closer display may be integrated with an input device the subject is using to provide input. In an effort to reduce devices a subject must maintain and handle, it may be advantageous for a touch-screen device that is capable of both displaying graphical elements and receiving a subject's input to be used in the performance of sensory testing and training.

Further, it may be desirable for a sensory stimulation device, such as a display or speaker, that is remote from a primary sensory testing and training device to communicate wirelessly with the primary testing and training device. The ability for a testing peripheral (e.g., sensory stimulation device) to be in communication with a controller (e.g., primary testing and training device) allows for a dynamic testing or training experience. For example, the sensory stimulus provided to the subject may be altered or changed based on the input provided by the subject. In order for the testing peripheral device to be dynamic, ongoing or intermittent communication between the controller and the peripheral device may be used. Wireless communication prevents frustrations and limitations that may be present if the peripheral device is tethered with cables or cords.

Embodiments of the present invention may be embodied as, among other things: a method, system, or set of instructions embodied on one or more computer-readable media. Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

Turning now to the figures, FIG. 1 illustrates a sensory testing and/or training system 100 in accordance with an embodiment of the present invention. System 100 includes a network 102, a sensory input touch device 104, a computing device 106, a display 108, and a testing peripheral 110.

The various components and devices may communicate with each other via the network 102, which may include, without limitation, one or more local area networks (LANs) and/or wide area networks (WANs). Additionally, in an exemplary embodiment, the network 102 operates in a peer-to-peer configuration. In an exemplary embodiment, the network 102 is comprised of both wired and wireless networks. The computing device 106, the display 108, and the testing peripheral 110 are coupled to a wired network while the sensory input touch device 104 communicates by way of a wireless network. Such networking environments are commonplace in offices, enterprise-wide computer networks, intranets, and the Internet.

The sensory input touch device 104 is a touch-screen device capable of receiving an input from a subject. For example, the sensory input touch device 104 may include a capacitive display screen that is capable of sensing one or more contacts that may be transformed into one or more indications of a subject's intent. A touch-screen device may implement a variety of techniques to identify a subject's input. For example, a touch screen may rely on technologies such as a resistive, a capacitive, a surface acoustic wave, infrared, strain gauge, dispersive signal technology, and acoustic pulse recognition. Generally, a touch-screen device is capable of displaying one or more graphical elements in an area that is functional to receive an input, such as a touch. An exemplary touch-screen device 104 may include an IPOD TOUCH available from the Apple Corporation of Cupertino, Calif. Similarly, an exemplary touch-screen device 104 may include gaming counsels (e.g., PLAYSTATION PORTABLE available from the Sony Computer Entertainment Inc. of Japan)

Additionally, the sensory input touch device is capable of communicating wirelessly with one or more components and devices of the system 100. For example, the sensory input touch device 104 is functional to communicate utilizing an Internet Protocol (IP) such as Transport Control Protocol (TCP) or User Datagram Protocol (UDP). UDP may be referred to as a Universal Datagram Protocol. UDP is a minimal message-oriented transport layer protocol that is documented in IETF RFC 768. Typically, UDP allows for a connectionless communication that facilitates quick communication of data. As a result, UDP may be desirable for a touch-screen device to use in the communication of user input to reduce system-induced latency. For example, it is desired to reduce system-induced latency resulting from a sensory test measuring reaction time where the computing device 106 instructs the sensory input touch device 104 to display a graphical image and the sensory input touch device 104 then must communicate back a user input in response to the graphical image. The subject's reaction time may be affected based on delays associated with communications between the sensory input touch device 104 and the computing device 106. Therefore, a protocol, such as UDP that minimizes system-induced latency may be advantageous.

The computing device 106 is a computing device comprised of a processor and memory. In an exemplary embodiment, the computing device 106 is coupled to the display 108 and the testing peripheral 110 to comprise a sensory testing and training device. The computing device 106 may control one or more graphical elements displayed by the display 108. The computing device may also facilitate the communication (outbound and inbound) of data between the sensory input touch device 104. For example, the computing device may instruct the sensory input touch device 104 to display one or more graphical elements, such as text, images, and symbols. Further, the computing device 106 may interpret user input or indication of intent received from the sensory input touch device 104. Additionally, the computing device may store data in an associated data store (not pictured).

The display 108 is a display for presenting a graphical element. For example, the display 108 may include a computer screen, a television monitor, three-dimensional displays, or a projector. In an exemplary embodiment, the display 108 is a high-resolution monitor capable of displaying vision testing and training graphical elements. In an exemplary embodiment, the display 108 may be moveably mounted to allow the display 108 to adjust to one or more desired heights relative to a subject. Further, the moveable mount may allow the display 108 to cover or expose an additional monitor located behind the monitor relative to a subject.

The testing peripheral 110 is a testing peripheral used in connection with a sensory test or sensory training activity. Examples of a testing peripheral may include a display, a load balancer (e.g., balance board, load sensor), motion capture technology equipment, motion simulating beams, etc. In an exemplary embodiment, a testing peripheral provides sensory stimulation in connection with a sensory test and/or a sensory training activity. Further, a testing peripheral may receive one or more subject inputs or sensory data. For example, a load balancer may monitor a subject's stability while one or more graphical elements are displayed by the display 108.

Figure 2:
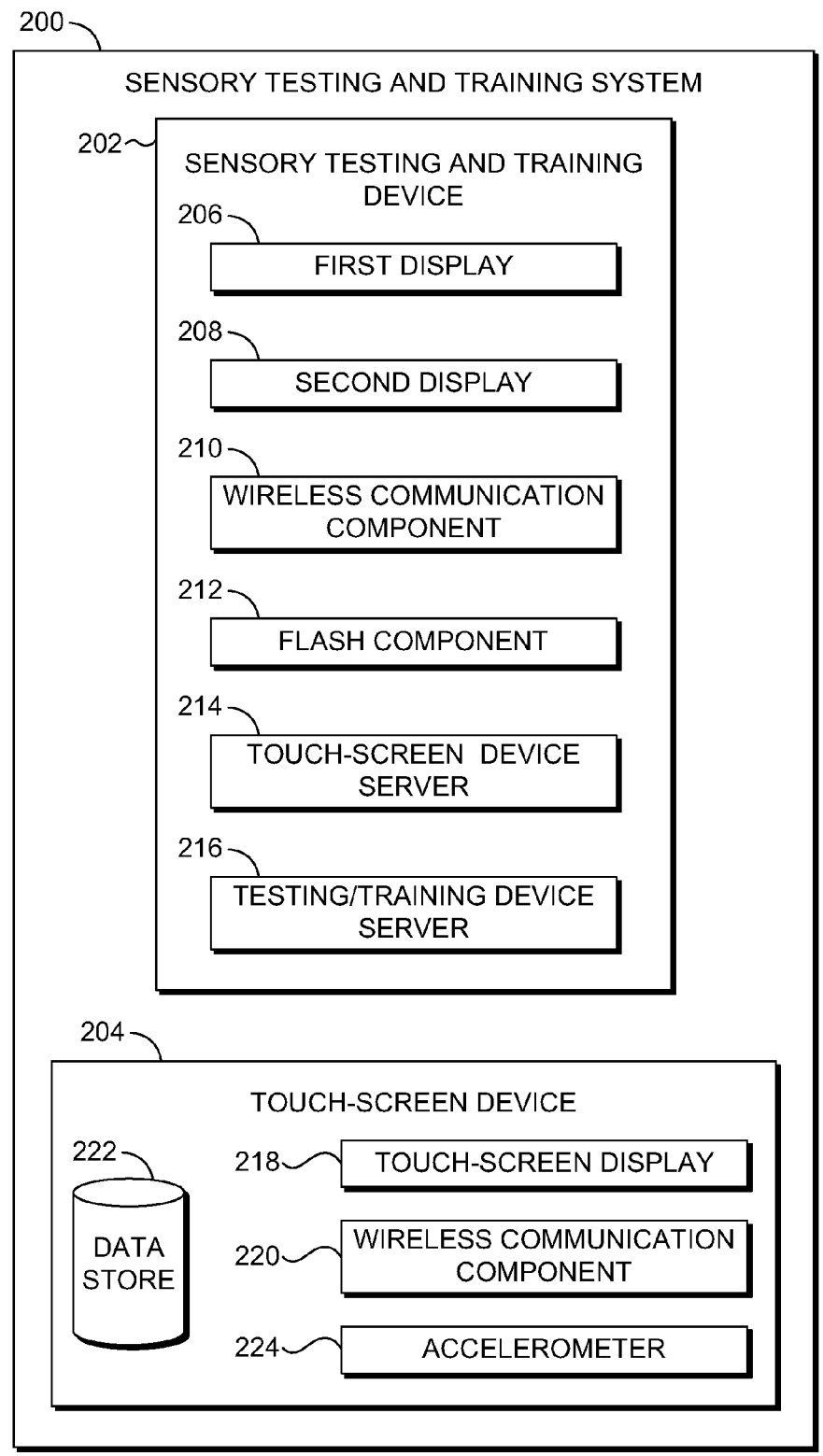
FIG. 2 illustrates an additional system in accordance with embodiments of the present invention.

Turning to FIG. 2 that illustrates an additional sensory testing and training system 200 in accordance with embodiments of the present invention. The system 200 includes a sensory testing and training device 202 and a touch-screen device 204. The system 200 is functional to test and train a subject's sensory abilities. For example, the system 200 may be functional to test aspects of a subject's visual abilities.

The sensory testing and training device 202 includes a first display 206, a second display 208, a wireless communication component 210, a flash component 212, a touch-screen device server 214, and a testing/training device server 216. The touch-screen device 204 includes a touch screen display 218, a wireless communication component 220, a data store 222, and an accelerometer 224.

The sensory testing and training device 202 is a device functional to administer a sensory test and/or a sensory training activity. For example, sensory testing and training device 202 may be utilized to administer a plurality of vision-related sensory tests to a subject. The administration may include providing sensory stimulus, receiving a subject's input, analyzing the subject's input, interpreting the subject's input, and storing the results associated with the administration.

The first display 206 and the second display 208 are displays for presenting one or more graphical elements. In an exemplary embodiment, the first display 206 and/or the second display 208 may be similar to the display 108 previously discussed with respect to FIG. 1. In an exemplary embodiment, the first display 206 is of a smaller dimension than the second display 208; however, the first display 206 is capable of displaying at a higher resolution than the second display 208. Therefore, it may be desirable for the first display 206 to be used for a particular sensory test and to use the second display 208 for other sensory tests. In yet an additional exemplary embodiment, the first display 206 is moveably mounted to the sensory testing and training device 202 to facilitate adjustment of a height at which it is located relative to the sensory testing and training device 202.

The wireless communication component 210 is a component for communicating, both receiving and sending, data to the touch-screen device 204. In an exemplary embodiment, the wireless communication component 210 is capable of communicating utilizing a protocol compatible with Bluetooth, which is a communication protocol and standard. Additionally, the wireless communication component 210 may be capable of communicating utilizing a protocol compatible with IEEE 802.11 standards (e.g., Wi-Fi). Therefore, in an exemplary embodiment, the sensory testing and training device 202 is capable of communicating wirelessly with the touch-screen device 204 utilizing, in part, the wireless communication component 210.

The flash component 212 is functional to compute, interpret, and/or translate information, data, and/or instructions in a flash based language format. For example, the flash component 212 may serve as an intermediary component between two servers/components that do not communicate using the same protocol or language, such as the touch screen device server 214 and the testing/training device server 216. The inclusion of the flash component 212 is not limiting on the scope of the present invention. For example, a flash compatible language may not be utilized at all or at least in the manner discussed herein. Therefore, while an embodiment of the present invention utilizes the flash component 212, the utilization of the flash component is not required. Additionally, it is contemplated that when a language other than flash is utilized in the communication between a touch-screen device and a testing/training device server, that a component (not shown in FIG. 2) is employed that facilitates computing, interpreting, and/or translating information, data, and/or instructions in the language format. For example, in an exemplary embodiment, a language compatible with JAVA, Silverlight, DirectX, etc. may be utilized, in whole or in part, to implement at least a portion of the functionality described herein for a multi-touch display/input device. Because languages other than flash may be implemented, it is understood that the flash component 212 may be supplemented and/or enhanced to provided the functionality discussed herein but with one or more additional languages being supported.

The touch-screen device server 214 is a computing device responsible for managing the touch-screen device 204. Management may include analyzing one or more data packets received from the touch-screen device 204. For example, the touch-screen device 204 may receive a subject's input that is interpreted at the touch-screen device 204 as an "up" command, and as a result the touch-screen device 204 may communicate data (e.g., "command=2") that signifies the subject's input was an up command. The touch-screen device server 214 may be responsible for determining the data signifies a particular subject input and identify what the input is intended to convey with respect to a sensory test or training activity. For example, when a visual indication is presented on the first display 206 and an input is determined to be provided by way of the touch screen device 204, the touch-screen device server 214 determines that input is in response to the visual indication displayed and interprets the input to be a particular response.

The testing/training device server 216 is a computing device functional to facilitate sensory testing and training utilizing the various components and devices of the sensory testing and training system 200. For example, the testing/training device server 216 may be responsible for administrative tasks associated with sensory testing and training. The administrative tasks may include controlling the first display 206, the storing of sensory data, the communication with the testing peripheral, controlling the flash component 212, etc.

The touch-screen display 218 is a touch screen capable of displaying a graphical element and receiving a subject's input through contact with a display surface. As previously discussed with respect to the sensory input touch device 104 of FIG. 1, a variety of technologies may be implemented to facilitate the desired functionality. For example, the touch-screen display 218 may use a capacitive touch-screen panel, which is coated with a material, typically indium tin oxide, which conducts a continuous electrical current across the sensor. The sensor may therefore exhibit a precisely controlled field of stored electrons in both the horizontal and vertical axes, which achieves capacitance. The human body is also an electrical device that has stored electrons and therefore exhibits capacitance. Capacitive sensors may work based on proximity and do not have to be directly touched to be triggered. Capacitive touch screens may also support multi-touch.

The wireless communication component 220, similar to the wireless communication component 210, facilitates wireless communication between the touch-screen device 204 and the sensory testing and training device. For example, the touch-screen device may communicate utilizing Bluetooth and/or Wi-Fi compatible technologies. It is understood that both uni-directional (e.g., communication going from the touch-screen device 204 to the sensory training and testing device 202) and bi-directional (e.g., communication originating at both the sensory testing and training device 202 and the touch-screen device 204 being communicated to the other device) communications are contemplated. Stated differently, it is contemplated that the touch-screen device 204 is functional for providing communications to and receiving communications from the sensory testing and training device 202.

The data store 222 is a data store for maintaining data. In an exemplary embodiment, the data store 222 includes one or more graphical elements to be displayed on the touch screen display 218. For example, the wireless communication component 220 may receive a command from the sensory testing and training system to display the graphical element. The touch-screen device 204 therefore retrieves the requested graphical element from the onboard data store 222. The local storage of the graphical elements reduces latency as the whole image is not required to be communicated wirelessly at each request, instead a mere pointer or reference may be communicated that is significantly smaller in size. Therefore, the request and resulting display of the graphical element may occur in an efficient manner. Additionally, the data store 222 may include one or more computer-readable media for controlling the touch-screen device with the utilization of a processor.

The accelerometer 224 is an accelerometer for identifying one or more acceleration forces. In an exemplary embodiment, the accelerometer 224 is functional to identify an orientation of the touch-screen device 204. For example, the touch-screen display 218 may provide visual information that is intended to be displayed at a particular orientation (e.g., textual elements that are intended to be displayed at the "top" of a display), utilizing the accelerometer 224 to measure gravity, a determination may be made as to what orientation the touch-screen device 204 is being held. Additionally, the accelerometer 224 is contemplated as providing an additional way of providing a user input. For example, instead of or in addition to, a user engaging the touch screen to provide an input, the accelerometer 224 may measure the directional movement of the touch-screen device 204 to identify a particular input provided by a user. For example, a user may move the touch-screen device in a direction in which the user desires to provide as an input. In an exemplary embodiment, directional portions, such as those discussed hereinafter at FIG. 5 with respect to a touch-screen device, may be employed in three-dimensional space to aid in identifying a user's intent when moving the touch-screen device.

In an additional exemplary embodiment, the sensory testing and training system 200 may include two or more touch-screen devices such as the touch-screen device 204. The two touch-screen devices may be used by two users to provide a competitive element to sensory testing or training. For example, a first touch-screen device may be used by a first user and a second touch-screen device may be used by a second user during one or more sensory training and/or testing activities to provide competitive incentive for the first and second user. Additionally, it is contemplated that sensory testing may be conducted as an individual activity while one or more sensory training activities are conducted as a joint activity. In addition to multiple touch-screen devices used as an input, the multiple touch-screen device may also provide feedback individually or in combination. For example, a first touch-screen device may provide a distraction (e.g., an audible alarm) that distracts not only a first user but also a second user.

Figure 3:
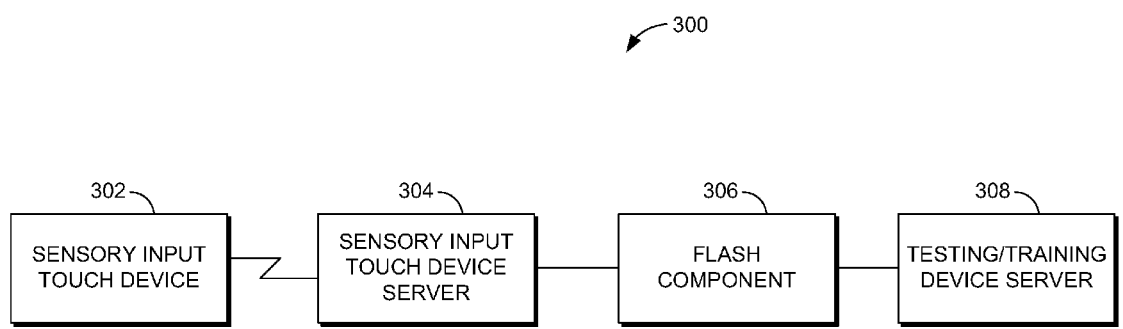
FIG. 3 illustrates an additional system in accordance with embodiments of the present invention.

Turning to FIG. 3 that illustrates an additional system 300 in accordance with embodiments of the present invention. The system 300 includes a sensory input touch device 302, a sensory input touch device server 304, a flash component 306, and a testing/training device server 308. The sensory input touch device 302, in an exemplary embodiment, is similar in disclosure to the touch-screen device 204 of FIG. 2. The sensory input touch device server 304, in an exemplary embodiment, is similar in disclosure to the touch-screen device server 214 of FIG. 2. The flash component, in an exemplary embodiment, is similar in disclosure to the flash component 212 of FIG. 2. The testing/training device server 308, in an exemplary embodiment, is similar in disclosure to the testing/training device server 216 of FIG. 2.

The sensory input touch device 302 communicates wirelessly with the sensory input touch device server 304. In an exemplary embodiment, the sensory input touch device 302 may include a touch-screen device as discussed herein. In an additional exemplary embodiment, the sensory input touch device 302 is located within sixteen feet of a sensory testing and training device. Additionally, in an exemplary embodiment, the sensory input touch device 302 is located within a range of twenty to four feet from a sensory testing and training device associated with the sensory input touch device server 304. In an additional exemplary embodiment, the distance at which the sensory input touch device 302 is located from a sensory testing and training device is a distance that achieves optical infinity for a user of the sensory input touch device 302. For example, a distance of sixteen to twenty feet from a visual object, for most users, provides a distance sufficient to achieve optical infinity for sensory testing and training purposes. Further, a distance of twenty feet provides one arc minute. In an exemplary embodiment, it is desirable for a user, and therefore the sensory input touch device 302, to be at a distance that provides at least fifteen arc seconds for a visual object. It is therefore contemplated that additional distance may be added to further test and train sensory abilities. For example, additional and/or less distance may be used when testing or training retinal disparity.

The sensory input touch device server 304 may receive the data communicated from the sensory input touch device 302 and interpret the data for use by a sensory testing and training device. The interpretation of the data may be communicated from the sensory input touch device server 304 to the flash component 306. The flash component 306 may include a library that supports the flash language, which may be a language relied upon, at least in part, for communicating among one or more computing devices. For example, the interpreted data may be further communicated to the testing/training device server 308 for analysis with respect to a sensory test or a sensory training activity.

Figure 4:
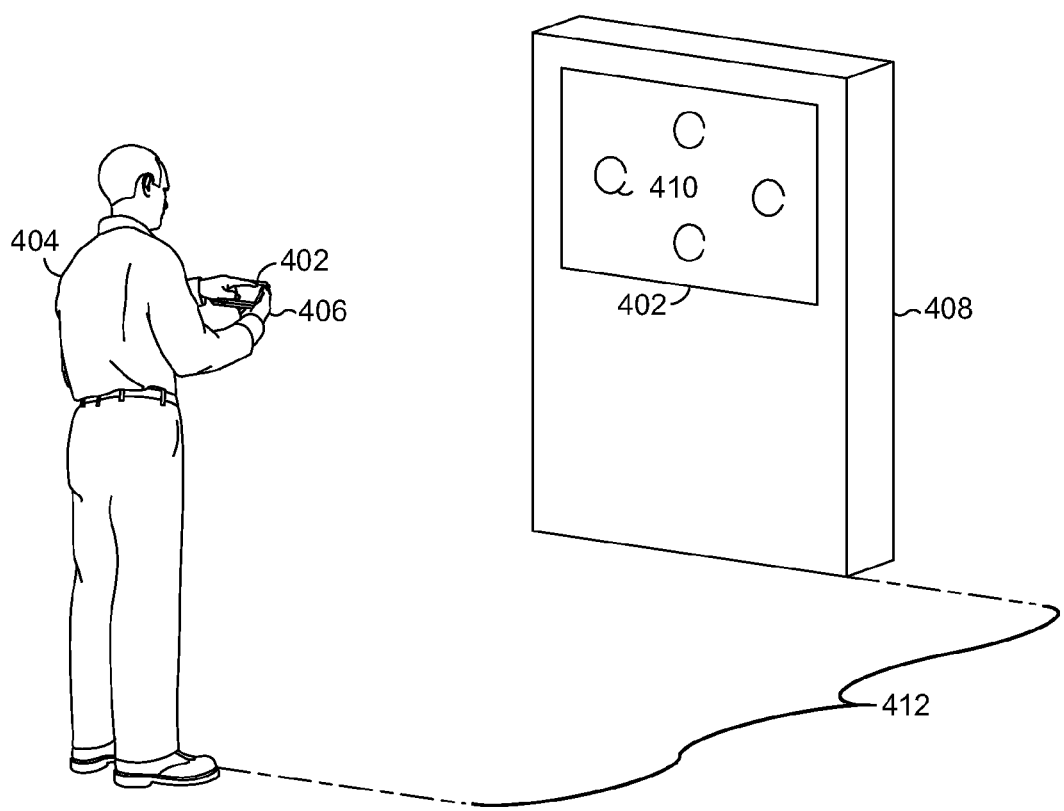
FIG. 4 illustrates a subject entering an input to a touch-screen device in response to a graphical element displayed from a sensory testing and training device in accordance with an exemplary embodiment of the present invention.

Turning to FIG. 4 that illustrates a subject 404 entering an input 406 to a touch-screen device 402 in response to a graphical element 410 displayed from a sensory testing and training device 408 in accordance with an exemplary embodiment of the present invention. In an exemplary embodiment, the subject 404 is positioned a predefined distance 412 from the sensory testing and training device 408. For example, one or more sensory testing and training activities may require the subject to be positioned a particular distance from the sensory testing and training device 408.

Because of the predefined distance 412, the touch-screen device 402 may communicate utilizing a wireless connection. In an exemplary embodiment, the wireless connection is advantageous in order to allow the subject to participate in a sensory test or training activity that may be hindered as a result of a tether or wired connection.

In an exemplary embodiment, the subject 404 is positioned the predefined distance 412 from the testing and training device 408 in order to participate in a sensory test or sensory training activity. The sensory testing and training device 408 displays, on a display, one or more graphical elements 410 that are intended to be perceived by the subject 404. Because of the subject's 404 perception of the graphical elements 410, the subject enters the input 406 into the touch-screen device 402. For example, when the subject desires to indicate a graphical element at the top of the display should be selected, the subject 404 may touch the touch-screen device in a manner prescribed by the touch-screen device to indicate a selection of the graphical element at the top.

Figure 5:
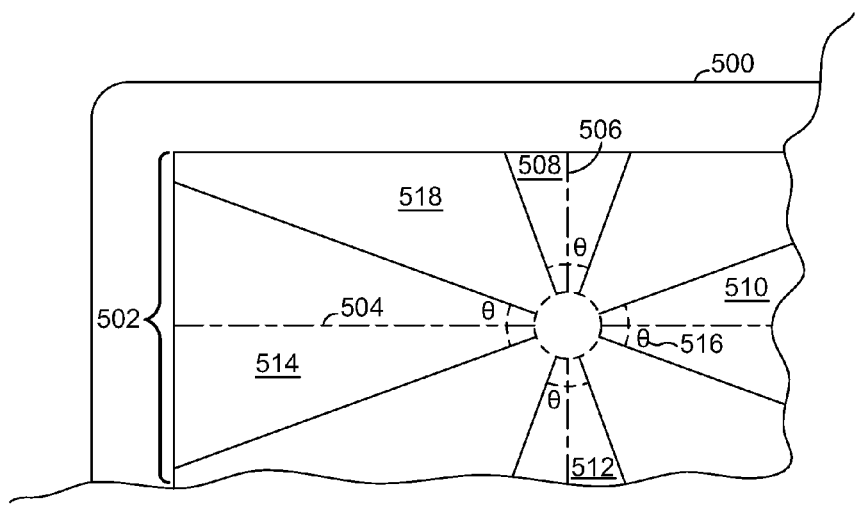
FIG. 5 illustrates a sensory input touch device in accordance with embodiments of the present invention.

Turning to FIG. 5 that illustrates a sensory input touch device 500 in accordance with embodiments of the present invention. The sensory input touch device 500 is a touch-screen device. The sensory input touch device 500 is comprised of a display surface 502. The display surface 502 is functional to display one or more graphical elements and receive a subject's input. The sensory input touch device 500 is illustrated with cut-away lines to illustrate that the sensory input touch device 500 is not limited to a particular size or shape. Further, the cut-away lines also illustrate that an origin, as discussed below, is not limited to a particular location or area of a sensory input touch device 500.

In an exemplary embodiment, the sensory input touch device 500 is functional to receive a subject's input in the form of a slide touch. A slide touch consists of contact being made at an initial point on the display surface 502 with contact being maintained across the display surface 502 to a second point. For example, a subject may place a finger at the center of the display surface 502 and drag the finger across the display surface 502 to the right. Such a drag may indicate a directional "right" input. It is understood that the "origin" of the display surface 502 may be at any point on the display surface 502. For example, the origin, in an exemplary embodiment, is located at a point of initial contact by a user. Therefore, the origin on which a directional input or other input is based may be at any location of the display surface 502.

In an embodiment, the direction of a drag is identified based on the degree from an orthogonal axis in which the contact travels. For example, contact that is maintained from a first point to a second point that is located to the right within 15 degrees from a horizontal axis of the display surface 502 is a directional "right" command. The display surface 502 may be comprised of an up portion 508, a right portion 510, a down portion 512, and a left portion 514. The portions center along one of the orthogonal axis 504 and 506. For example, the down portion 512 is centered on the vertical axis 506. The down portion 512 radiates from an origin at a predefined degree 516. The predefined degree 516 is an angle at which the down portion 512 extends from the axis on which it is centered (i.e., vertical axis 506). The predefined degree 516 may also be expressed relative to the axis dissecting an associated portion; therefore, an angle within a certain number of degrees of an axis represents a predefined angle twice the number presented. For example, if a right indication may be expressed with a movement within 7.5 degrees of the horizontal orthogonal axis 504, then a predefined angle of 15 degrees is used as it includes both 7.5 degrees above and below the axis. It is contemplated that the orientation of the input touch device 500 may determine what portion coincides with a particular direction. For example, if the input touch device 500 is in a rectangular shape, when the device is oriented in a portrait manner, the "up" portion may coincide with the upper short side of the rectangle. While, if the device is oriented in a landscape manner, then the upper long side of the rectangle may coincide with the "up" portion.

In an exemplary embodiment, portions, such as the up portion 508, the right portion 510, the down portion 512, and the left portion 514 are nonoverlapping portions that do not share a common point on the display surface 502. However, it is appreciated that an origin point at which an initial point of contact is made is an area that may be common to two or more of the portions because it is an intersection of various portions. Additionally, the origin may include a predefined radius extending from the initial point of contact in which no one portion is identified as being exclusive to that area. Further, the display surface may include one or more noninput portions, such as portion 518. Portion 518 is a portion that is located between the up portion 508 and the left portion 514. In an exemplary embodiment, an input identified as being associated with the portion 518 is a null input that is not associated with a direction. For example, an input that is identified as being in the portion 518 falls outside of a level of confidence that the input is intended to be associated with either the up portion 508 or the left portion 514. Therefore, noninput portions may exist between various input portions to provide confidence that a sensed input has a particular intent.

Further, in an exemplary embodiment, the predefined angle that defines one or more of the portions provides a range in which a user may enter an input. For example, in order to compensate for inaccuracies in holding an input device or inaccuracies of the user providing an input, the range as defined by an angle allows for the input to deviate from a precise axial movement. Therefore, if a user is not holding the input touch device in an apparent alignment with a customary level position, then a customary user input in an "up" direction would not correspond with the vertical axis 506. However, because the "up" portion 508 is defined by an angle theta, a user input may be identified as being an "up" input when the input is within the "up" portion 508. Further, because a user may not be concerned with providing precise or exact directional indications, a range defined by an angle (e.g., angle 516) allows for imprecision and unexactness of an input.

In an exemplary embodiment, an origin defined by the intersection of the orthogonal axis 504 and 506 is positioned at an initial point of contact on the display surface 502. Therefore, regardless of the initial point of contact, the directional intent of a subject may be determined. While the various portions (e.g., 508, 510, 512, 514) are not displayed by the sensory input touch device 500 in an exemplary embodiment, they are illustrated herein to provide clarity to the discussion. In an additional embodiment, one or more portions or visual elements may be displayed to aid a subject in providing an input consistent with the subject's intention.

Additionally, in an exemplary embodiment, one or more tactile guides may be associated with the input touch device 500. For example, a protective cover may encase the input touch device 500 that provides an opening for the display surface 502 to be contacted by a user. The opening provided by the protective case may be limited to an active or useable area of the display surface 502. Additionally, one or more linear, polygonal, or curvilinear surfaces may be coupled to the input touch device 500 in order to provide tactile indications as to orientation, useable area, or axial locations of the input touch device 500.

The input touch device 500 may also include an audible emitter, such as a speaker. The audible emitter may produce one or more sounds, such as feedback to a user. The sounds may be used to provide interference, distractions, or information for use in the sensory training and/or testing.

Figure 6:
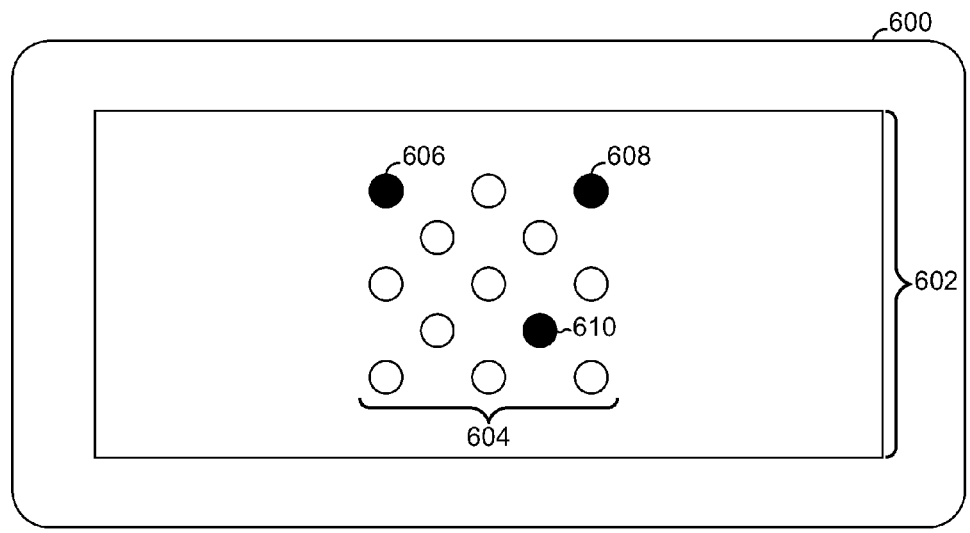
FIG. 6 illustrates a second sensory input touch device in accordance with an exemplary embodiment of the present invention.

Turning to FIG. 6 that illustrates a second sensory input touch device 600 in accordance with an exemplary embodiment of the present invention. The sensory input touch device 600 includes a display surface 602 that is functional to display one or more graphical elements 604. For example, sensory input touch device 600 displays elements 606, 608, and 610. The elements 606-610 are visually present on the display surface 602 as part of a sensory testing or sensory training activity. In an exemplary embodiment, a subject contacts the sensory input touch device 600 at locations relative to each of the points 606-610 as an input. For example, an external display associated with a sensory testing and training device that is a predefined distance from the subject may display three graphical elements at locations that coincide with the graphical elements 606-610 selected by the subject. Therefore, the sensory input touch device 600 may display one or more graphical elements to aid in the subject providing an input. Additionally, the sensory input touch device 600 may display one or more graphical elements as part of a sensory test or a sensory training activity.

Figure 7:
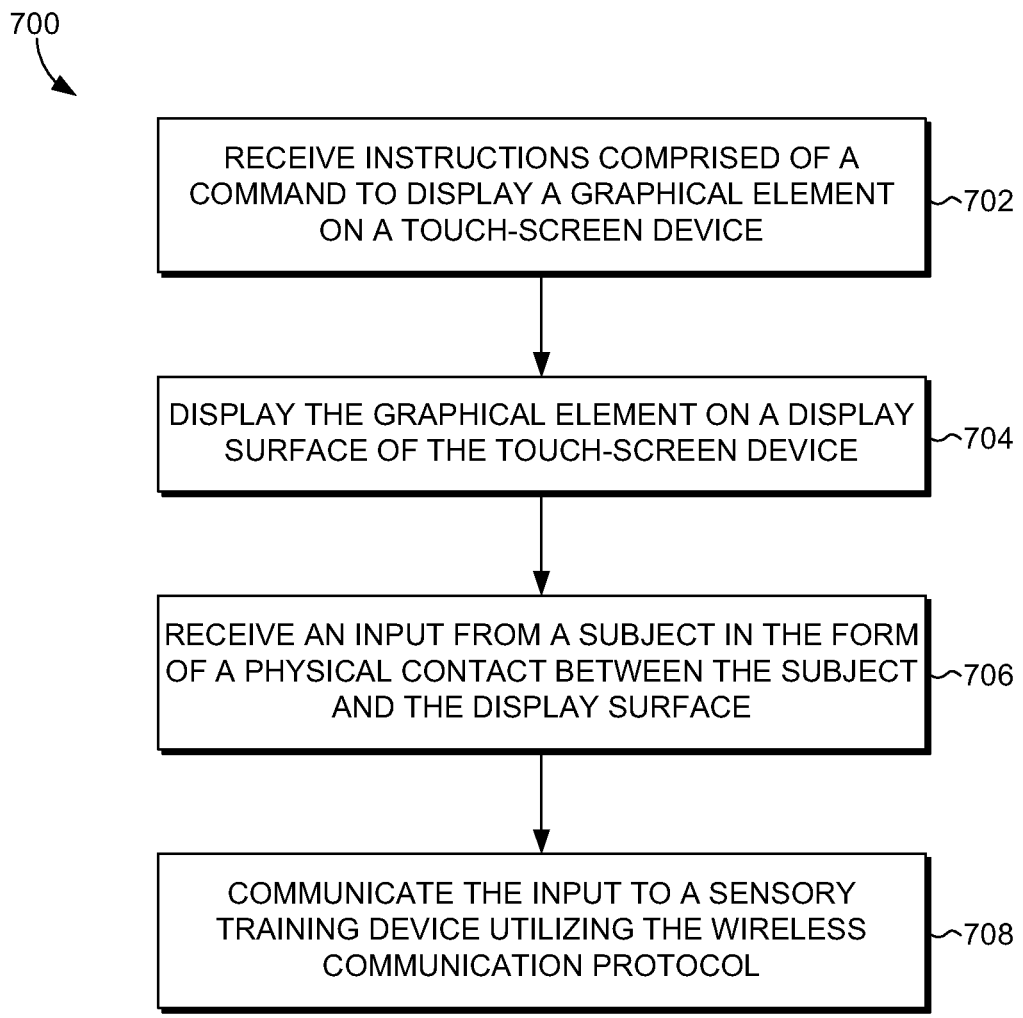
FIG. 7 illustrates a block diagram depicting a method for receiving an input to a sensory test by way of a touch-screen device utilizing a computing device having memory and a processor in accordance with an embodiment of the present invention.

Turning to FIG. 7 that illustrates a block diagram depicting a method 700 for receiving an input to a sensory test by way of a touch-screen device utilizing a computing device having memory and a processor in accordance with an embodiment of the present invention. At a step 702, a touch-screen device receives instructions comprised of a command to display a graphical element. For example, a sensory testing and training device may desire for instructional or tutorial information to be displayed on the touch-screen device. Additionally, a graphical element representing a start command may be displayed by the touch-screen device. In an exemplary embodiment, the graphical element is stored within the touch-screen device and the graphical element is accessed as a result of the command. For example, the instructions may include computer executable code that includes a command to display a particular image file stored within the touch-screen device. At a step 704, the touch-screen device displays the graphical element on a display surface. For example, the graphical element may be rendered from a data file. In an exemplary embodiment, the instructions are received by way of a wireless communication protocol.

At a step 706, the touch-screen device receives an input from a subject in the form of a physical contact between the subject and the display surface. For example, a subject may desire to provide a particular command as a result of one or more sensory stimulations presented as part of sensory testing or training, and as a result, the subject makes contact with the touch-screen device to signal an input.

At a step 708, the touch-screen device communicates the input to a sensory training device utilizing a wireless communication protocol. In an exemplary embodiment, the touch-screen device communicates an interpreted command from the input. For example, the touch-screen device analyzes the input from the subject and determines the intent of the subject based on one or more predefined criteria, rules, and/or tolerances.

Figure 8:
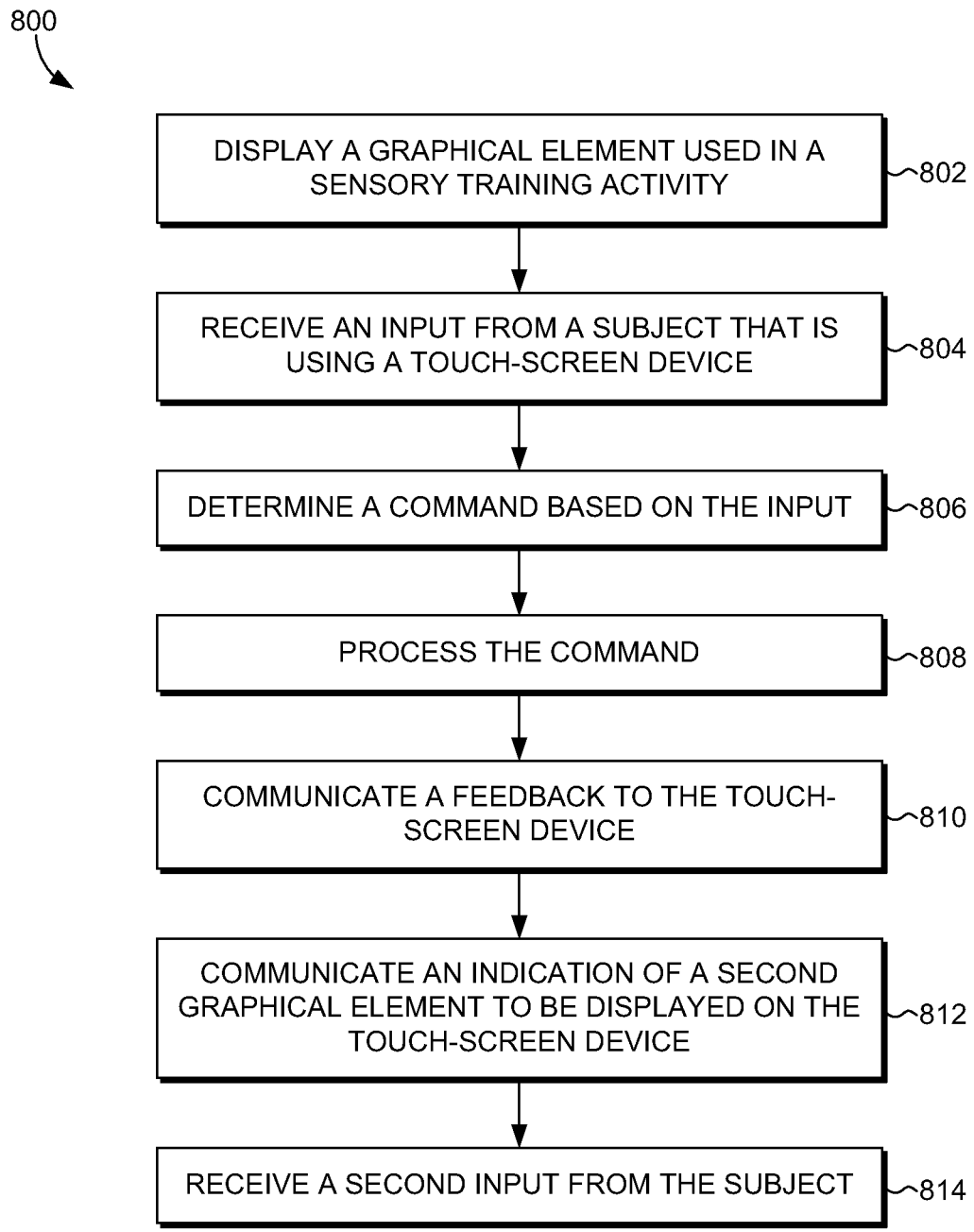
FIG. 8 illustrates a block diagram depicting a method for wirelessly receiving an input in response to a sensory training activity from a subject at a touch-screen device in accordance with an exemplary embodiment of the present invention.

Turning to FIG. 8 that illustrates a block diagram depicting a method 800 for wirelessly receiving an input in response to a sensory training activity from a subject at a touch-screen device in accordance with an exemplary embodiment of the present invention. At a step 802, a sensory training device displays a graphical element used as part of a sensory training activity. At a step 804, the sensory training device receives an input from a subject that is using a touch-screen device. For example, in response to the graphical element displayed at the step 802, a subject may provide a response, which is entered into a touch-screen device by the subject making contact with the touch-screen device. The touch-screen device in this example may then wirelessly communicate the input to the sensory training device.

At a step 806, the sensory training device determines a command based on the input. For example, the input may be in a format effectively communicated by way of a wireless communication protocol, but the input is not in a format useable in the analysis of sensory training results, therefore the input is interpreted to a command that is useable by the sensory training device. For example, a numerical indicator may be communicated from the touch-screen device as an input. The numerical indicator is interpreted to represent a particular directional input (e.g., right, left, up, down). At a step 808, the command is processed. For example, the command is processed by a computing device of the sensory training device to provide a result that may be analyzed relative to the graphical element previously displayed.

At a step 810, the sensory training device communicates a feedback to the touch-screen device. For example, upon the successful processing of the command, a confirmation feedback may be communicated to the touch-screen device. In an exemplary embodiment, the feedback includes a command to produce an audible tone that represents the input has been received and processed. In an additional embodiment, the feedback may be an instruction to display a particular graphical element at the touch-screen device. Further, the feedback may include tactile feedback such as a vibratory sensation or other vibration-type input. For example, upon successful interpretation of an input command, the touch-screen device may vibrate in a first manner to indicate successful interpretation of an input. Additionally, it is contemplated that various vibrations (e.g., pulses, constant, intermittent, any combination thereof) may be utilized to indicate various meanings. For example, on a time exercise a low-time warning may be provided a second vibration type, an incorrect response may be a third vibration type, and a correct response is a fourth vibration type. Further, it is contemplated that combinations of feedback may be employed. For example, audible tones may be provided for correct feedback, vibrations may be provided for incorrect feedback, and a combination of vibration and audible feedback may be provided for expiration or completion of an activity.

At a step 812, an instruction is communicated from the sensory training device to the touch-screen device. The instruction is a command to display a graphical element on the touch-screen device. For example, the touch-screen device may display a graphical element used as part of a sensory training activity (e.g., training object, instructions, input guides). At a step 814, the sensory training device receives a second input from the subject. For example, in response to the graphical element displayed at the touch-screen device, the subject may provide input.

Various methods have been described herein; it is contemplated that one or more of the methods may be implemented in a computing environment by one or more computing devices having processors and memory. Therefore, while certain methods were not discussed with respect to a computing environment, the methods may additionally be implemented in a computing environment using one or more computing devices.

The present invention has been described herein in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well-adapted to attain the ends and objects set forth above, together with other advantages that are obvious and inherent to the methods. It will be understood that certain features and subcombinations are of utility and may be employed without reference to other features and subcombinations. This is contemplated by and within the scope of the claims.

The invention claimed is:

1. A method for receiving an input to a vision sensory activity by way of a hand-held touch-screen device having memory and a processor, the method comprising:

displaying a first graphical element of the vision sensory activity at a first display on a sensory testing and training device, wherein the sensory testing and training device is a physically separate device from the touch-screen device, and wherein the first display is at a first distance from a user;

receiving instructions from the sensory testing and training device at the touch-screen device by way of a wireless communication protocol, wherein the instructions are comprised of a command to display a second graphical element of the vision sensory activity on the touch-screen device, wherein the touch screen device is at a second distance from the user, and the second graphical element is displayed on a display surface of the touch-screen device to aid the user in providing input, wherein the display surface of the touch-screen device is functional to receive the input from the user in the form of a directional drag such that the display surface of the touch-screen device comprises an origin and one or more null input portions disposed between directional input portions to provide confidence that a sensed input has a particular intent, and wherein the directional input portions are associated with the directional drag and the null input portions are not associated with the directional drag;

receiving an input from the user that is engaged in a vision sensory test or a vision sensory training activity corresponding to the vision sensory activity, the input being in the form of a physical contact between the user and the display surface of the touch screen-device, wherein the input is in response to the vision sensory activity that involves at least the first graphical element displayed to the subject on the first display at the sensory testing and training device;

identifying the input as a directional drag based on a touch input that is maintained from a point of initial contact by the user to a subsequent point of contact by the user along an orthogonal axis corresponding to at least one of the directional input portions, wherein the point of initial contact by the user comprises the origin and a predefined radius extending from the initial point of contact in which no one portion is defined as being exclusive to an area inside the predefined radius; and communicating the input to the sensory testing and training device utilizing the wireless communication protocol.

2. The method of claim 1 further comprises determining an intent associated with the input.

3. The method of claim 2, wherein the intent comprises one from the following:
an up indication,
a down indication,
a left indication, and
a right indication.

4. The method of claim 3, wherein the intent is determined based on the reception of the input within a predefined number of degrees from an intent direction.

5. The method of claim 3, wherein the intent is determined based on the reception of the input within about 7.5 degrees from an intent direction.

6. The method of claim 1, wherein the wireless communication protocol utilizes an Internet Protocol (IP) compatible protocol.

7. The method of claim 6, wherein the IP compatible protocol is compatible with a User Datagram Protocol (UDP).

8. The method of claim 1, wherein the input in response to the vision sensory activity visually presented by the sensory testing and training device, further comprises input from an accelerometer provided in the touch-screen device.

9. The method of claim 1, wherein the input is in response to a vision sensory activity visually presented by a combination of the touch-screen device and the sensory testing and training device.

10. A sensory testing and training system comprising:
a sensory testing and training device located at a first distance from a subject, the sensory testing and training device having a processor, a first display for displaying one or more graphical elements associated with a vision sensory activity, and memory for facilitating the vision sensory activity, wherein the sensory testing and training device is comprised of a wireless communication component for communicating with a physically separate hand-held touch-screen device;
the touch-screen device located at a second distance from the subject, wherein the second distance is less than the first distance, the touch-screen device having a processor and memory for receiving an input from the subject in response to the vision sensory activity involving at least the one or more graphical elements displayed to the subject on the first display, wherein the touch-screen device comprises a second display separate from the first display, and wherein the touch-screen device receives instructions from the sensory testing and training device by way of the wireless communication component to display another graphical element of the vision sensory activity on the second display, wherein the another graphical element is displayed on the second display to aid the subject in providing input;
wherein the second display is functional to receive the input from the subject in the form of a physical contact between the subject and the second display in response to the vision sensory activity, wherein the input is in the form of a directional drag such that the second display comprises an origin and one or more null input portions disposed between directional input portions to provide confidence that a sensed input has a particular intent, and wherein the directional input portions are associated with the directional drag and the null input portions are not associated with the directional drag; and
wherein the touch-screen device identifies the input as a directional drag based on a touch input that is maintained from a point of initial contact by the subject to a subsequent point of contact by the subject along an orthogonal axis corresponding to at least one of the directional input portions, wherein the point of initial contact by the subject comprises the origin and a predefined radius extending from the initial point of contact in which no one portion is defined as being exclusive to an area inside the predefined radius.

11. The system of claim 10, wherein the touch-screen device is functional to receive a multitouch input from the subject.

12. The system of claim 10, wherein the second display of the touch-screen device is a capacitive touch screen, wherein the capacitive touch screen is functional for receiving the input and displaying the another graphical element.

13. The system of claim 10, wherein the touch-screen device and the sensory testing and training device communicate utilizing a protocol compatible with Internet Protocol (IP).

14. The system of claim 10, wherein the touch-screen device and the sensory testing and training device communicate utilizing a User Datagram Protocol (UDP).

15. The system of claim 10, wherein the touch-screen device and the sensory testing and training device are separated by at least three feet.

16. The system of claim 10, wherein the sensory testing and training device is further comprised of:
a third display for displaying one or more graphical elements associated with the vision sensory activity, wherein the third display is moveably mounted to the sensory testing and training device; and
wherein either the first display or the third display present a graphical element to the subject as part of the vision sensory activity to which the subject provides an input by way of the touch-screen device.

17. One or more non-transitory computer-readable media having computer-executable instructions embodied thereon for wirelessly receiving an input in response to a vision sensory activity via a wireless communication protocol, the vision sensory activity involving at least a graphical element displayed to a subject on a sensory testing and training device and the input from the subject on a hand-held touch-screen device, the method comprising:
on a first display moveably mounted to the sensory testing and training device, physically separated from the touch-screen device and at a first distance from the subject, displaying to the subject the graphical element used in the vision sensory activity;

receiving instructions from the sensory testing and training device at the touch-screen device by way of the wireless communication protocol to display a second graphical element of the vision sensory activity on a second display of the touch-screen device, the second graphical element being displayed to aid the subject in providing input;

receiving the input from the subject at the touch-screen device, the touch-screen device at a second distance from the subject that is less than the first distance, wherein the second display is functional to receive the input from the subject in the form of a directional drag such that the second display comprises an origin and one or more null input portions disposed between directional input portions to provide confidence that a sensed input has a particular intent, and wherein the directional input portions are associated with the directional drag and the null input portions are not associated with the directional drag, wherein the input is a physical contact between the subject and the second display and the input is in response to the vision sensory activity that involves at least the first graphical element displayed to the subject on the first display at the sensory testing and training device, and wherein the input is identified as a directional drag based on a touch input that is maintained from a point of initial contact by the subject to a subsequent point of contact by the subject along an orthogonal axis corresponding to at least one of the directional input portions, wherein the point of initial contact comprises the origin and a predefined radius extending from the initial point of contact in which no one portion is defined as being exclusive to an area inside the predefined radius;

determining a command based on the input;

processing the command;

communicating a feedback to the touch-screen device, wherein the feedback is processed by the touch-screen device to provide visual, audible, or tactile feedback to the subject in response to the input; and receiving a subsequent input from the subject, wherein the subsequent input is responsive to a displayed subsequent graphical element used in the vision sensory activity.

18. The media of claim 17, wherein the particular intent comprises one from the following:
   an up indication,
   a down indication,
   a left indication, and
   a right indication.

19. The media of claim 17, wherein the wireless communication protocol utilizes an Internet Protocol (IP) compatible protocol.

* * * * *